United States Patent [19]

Rheinheimer et al.

[11] Patent Number: 5,360,913
[45] Date of Patent: Nov. 1, 1994

[54] SALICYCLIC ACID DERIVATIVES

[75] Inventors: Joachim Rheinheimer, Ludwigshafen; Karl Eicken, Wachenheim; Uwe J. Vogelbacher, Ludwigshafen; Karl-Otto Westphalen, Speyer; Matthias Gerber, Mutterstadt; Helmut Walter, Obrigheim, all of Germany

[73] Assignee: BASF Aktiengesellschaft, Ludwigshafen, Germany

[21] Appl. No.: 64,917

[22] Filed: May 24, 1993

Related U.S. Application Data

[62] Division of Ser. No. 994,253, Dec. 21, 1992, abandoned, which is a division of Ser. No. 778,318, Oct. 16, 1991, Pat. No. 5,201,937.

[30] Foreign Application Priority Data

Oct. 26, 1990 [DE] Germany .......................... 4034045

[51] Int. Cl.$^5$ .................. C07D 249/04; C07D 249/08
[52] U.S. Cl. ................................ 548/255; 548/266.8; 548/341.5; 548/369.4; 548/547
[58] Field of Search ............ 548/545, 547, 255, 262.2, 548/373, 378, 369, 335, 341.5, 375, 369.4, 547, 266.8

[56] References Cited

U.S. PATENT DOCUMENTS 5,185,027 2/1993 Vogelbacher et al. ............. 544/219
5,201,937 4/1993 Rheinheimer et al. ............. 544/219

Primary Examiner—John M. Ford
Assistant Examiner—Pavanaram K. Sripada
Attorney, Agent, or Firm—Keil & Weinkauf

[57] ABSTRACT

Salicylic acid derivatives of the formula I

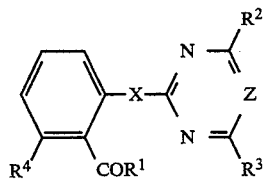

($R^1$ is succinimidoxy; unsubstituted or substituted hetaryl; $OR^5$ where $R^5$ is substituted or unsubstituted cycloalkyl, alkyl, alkenyl, alkynyl, phenyl or substituted methyleneamino; $OR^8$ where $R^8$ is hydrogen, alkali metal or alkaline earth metal cation, ammonium or organic ammonium;
$R^2$ and $R^3$ are each $C_1$-$C_4$-alkyl, $C_1$-$C_2$-haloalkyl, $C_1$-$C_4$-alkoxy or $C_1$-$C_2$-haloalkoxy and/or $C_1$-$C_4$-alkylthio;
$R^4$ is ethynyl or unsubstituted or substituted vinyl;
X is oxygen or sulfur;
Z is nitrogen or methine)
are used as herbicides and bioregulators.

2 Claims, No Drawings

SALICYCLIC ACID DERIVATIVES

This is a division of application Ser. No. 07/994,253, now abandoned filed Dec. 21, 1992, which was a division of application Ser. No. 07/778,318, filed Oct. 10, 1994 now U.S. Pat. No. 5,201,937.

The present invention relates to salicylic acid derivatives of the formula I

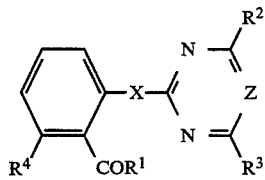

where
R$^1$ is succinimidoxy;
a 5-membered heteroaromatic radical which contains two or three nitrogen atoms and which can carry one or two halogen atoms and/ or one or two of the following: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;
—OR$^5$ where
R$^5$ is $C_3$–$C_{12}$-cycloalkyl which can carry one to three $C_1$–$C_4$-alkyl radicals; $C_1$–$C_{10}$-alkyl which can carry one to five halogen atoms and/or one of the following:
$C_1$–$C_4$-alkoxy, $C_1$–$C_4$-alkylthio, cyano, $C_1$–$C_8$-alkylcarbonyl, $C_3$–$C_{12}$-cycloalkyl, $C_1$–$C_8$-alkoxycarbonyl, phenyl, phenoxy or phenylcarbonyl, it being possible for the aromatic radicals in turn to carry one to five halogen atoms and/or one to three of the following: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;
$C_2$–$C_6$-alkyl which carries in position 2 one of the following: $C_1$–$C_6$-alkoxyimino, $C_3$–$C_6$-alkenyloxyimino, $C_3$–$C_6$-haloalkenyloxyimino or benzyloxyimino;
$C_3$–$C_6$-alkenyl or $C_3$–$C_6$-alkynyl, each of which in turn can carry one to five halogen atoms; phenyl which is unsubstituted or substituted one to three times by $C_1$–$C_4$-alkyl or $C_1$–$C_4$-alkoxy or one to five times by halogen; or
—N=CR$^6$R$^7$ where
R$^6$ and R$^7$ are each $C_1$–$C_{20}$-alkyl which can carry phenyl, $C_1$–$C_4$-alkoxy and/or $C_1$–$C_4$-alkylthio, or are phenyl or together form a $C_3$–$C_{12}$-alkylene chain which can carry one to three $C_1$–$C_3$-alkyl groups;
or
—OR$^8$ where
R$^8$ is hydrogen, an alkali metal cation, the equivalent of an alkaline earth metal cation, ammonium or an organic ammonium ion;
R$^2$ and R$^3$ are each $C_1$–$C_4$-alkyl, $C_1$–$C_2$-haloalkyl, $C_1$–$C_4$-alkoxy, $C_1$–$C_2$-haloalkoxy and/or $C_1$–$C_4$-alkylthio;
R$^4$ is ethynyl or vinyl which can carry one to three halogen atoms;
X is oxygen or sulfur;
Z is nitrogen or =CH—.

The present invention also relates to processes for preparing these compounds, to the use thereof as herbicides and growth regulators, and to compounds of the formula IV

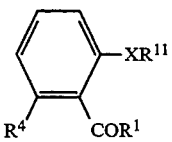

as intermediates for preparing compounds I where R$^{11}$ is hydrogen, acetyl or methyl.

Aromatic carboxylic acid derivatives with herbicidal activity are described in EP-A 223 406, 287 072, 287 079, 249 708 and 360 163. However, they contain no ethynyl or vinyl substituents and their herbicidal action is unsatisfactory.

It is an object of the present invention to provide other, particularly effective compounds with improved herbicidal properties and with growth-regulating properties.

We have found that this object is achieved by the compounds I defined above.

We have also found processes for preparing the compounds I, intermediates of the formula IV, herbicidal agents containing the compound I, methods for controlling unwanted plant growth, the use of the compounds I as herbicides, and agents for influencing and methods for controlling plant growth.

With a view to the intended use of the salicylic acid derivatives as herbicides and growth regulators, the preferred substituents are the following:
R$^1$ succinimidoxy;
5-membered hetaryl such as pyrrolyl, pyrazolyl, imidazolyl and triazolyl, especially imidazolyl and pyrazolyl, where the aromatic radical is bonded via nitrogen and can in turn carry one or two halogen atoms, especially fluorine and chlorine and/or one or two of the following:
$C_1$–$C_4$-alkyl such as methyl, ethyl, propyl, 1-methylethyl, butyl, 1-methylpropyl, 2-methylpropyl and 1,1-dimethylethyl, preferably methyl, ethyl and 1-methylethyl;
$C_1$–$C_4$-haloalkyl, preferably $C_1$–$C_2$-haloalkyl such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl and pentafluoroethyl, especially difluoromethyl, trifluoromethyl, 2,2,2-trifluoroethyl and pentafluoroethyl;
$C_1$–$C_4$-alkoxy such as methoxy, ethoxy, propoxy, 1-methylethoxy and butoxy;
$C_1$–$C_4$-haloalkoxy, especially $C_1$–$C_2$-haloalkoxy such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, especially trifluoromethoxy and/or
$C_1$–$C_4$-alkylthio such as methylthio, ethylthio, propylthio, 1-methylethylthio, butylthio, 1-methylpropylthio, 2-methylpropylthio and 1,1-dimethylethylthio, especially methylthio and ethylthio;

—OR⁵ where R⁵ preferably has the following meaning:

$C_3$–$C_6$-cycloalkyl such as cyclopropyl, cyclobutyl, cyclopentyl and cyclohexyl, which can carry one to three $C_1$–$C_4$-alkyl radicals, especially methyl and ethyl;

$C_1$–$C_{10}$-alkyl such as methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 2-methylhexyl, 3-methylhexyl, 4-methylhexyl, 5-methylhexyl, 1-ethylpentyl, 2-ethylpentyl, 1-propylbutyl, octyl, nonyl and decyl, preferably $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, which for $C_1$ can carry one to three, and for $C_2$–$C_{10}$ can carry one to five, halogen atoms, especially fluorine and chlorine and/or one of the following:

$C_1$–$C_4$-alkoxy, especially methoxy, ethoxy and 1-methylethoxy;

$C_1$–$C_4$-alkylthio, especially methylthio and ethylthio; cyano;

$C_1$–$C_6$-alkylcarbonyl such as methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl and 1-ethyl-2-methylpropylcarbonyl;

$C_3$–$C_6$-cycloalkyl such as cyclopropyl, cyclopentyl and cyclohexyl;

$C_1$–$C_8$-alkoxycarbonyl such as methoxycarbonyl, ethoxycarbonyl, propyloxycarbonyl, 1-methylethoxycarbonyl, butyloxycarbonyl, 1-methylpropyloxycarbonyl, 2-methylpropyloxycarbonyl, 1,1-dimethylethoxycarbonyl, n-pentyloxycarbonyl, 1-methylbutyloxycarbonyl, 2-methylbutyloxycarbonyl, 3-methylbutyloxycarbonyl, 1,2-dimethylpropyloxycarbonyl, 1,1-dimethylpropyloxycarbonyl, 2,2-dimethylpropyloxycarbonyl, 1-ethylpropyloxycarbonyl, n-hexyloxycarbonyl, 1-methylpentyloxycarbonyl, 2-methylpentyloxycarbonyl, 3-methylpentyloxycarbonyl, 4-methylpentyloxycarbonyl, 1,2-dimethylbutyloxycarbonyl, 1,3-dimethylbutyloxycarbonyl, 2,3-dimethylbutyloxycarbonyl, 1,1-dimethylbutyloxycarbonyl; 2,2-dimethylbutyloxycarbonyl, 3,3-dimethylbutyloxycarbonyl, 1,1,2-trimethylpropyloxycarbonyl, 1,2,2-trimethylpropyloxycarbonyl, 1-ethylbutyloxycarbonyl, 2-ethylbutyloxycarbonyl, 1-ethyl-2-methylpropyloxycarbonyl, n-heptyloxycarbonyl, 1-methylhexyloxycarbonyl, 2-methylhexyloxycarbonyl, 3-methylhexyloxycarbonyl, 4-methylhexyloxycarbonyl, 5-methylhexyloxycarbonyl, 1-ethylpentyloxycarbonyl, 2-ethylpentyloxycarbonyl, 1-propylbutyloxycarbonyl and octyloxycarbonyl, especially $C_1$–$C_4$-alkoxycarbonyl, such as methoxycarbonyl, ethoxycarbonyl, propoxycarbonyl, 1-methylethoxycarbonyl and 1-methylpropoxycarbonyl, phenyl, phenoxy, phenylcarbonyl, 2-, 3- or 4-fluorophenyl, 2-, 3- or 4-chlorophenyl, 2-, 3- or 4-methylphenyl, 2-, 3- or 4-methylphenoxy, 2-, 3- or 4-methylphenylcarbonyl, 2-, 3- or 4-trifluoromethylphenyl, 2-, 3- or 4-trifluoromethylphenoxy, 2-, 3- or 4-trifluoromethylphenylcarbonyl, 2-, 3- or 4-methoxyphenyl, 2-, 3- or 4-methoxyphenoxy, or 2-, 3- or 4-methylthiophenyl;

$C_2$–$C_6$-alkyl, especially $C_2$–$C_4$-alkyl, which is substituted in position 2 by $C_1$–$C_6$-alkoxyimino, especially $C_1$–$C_4$-alkoxyimino such as methoxy-, ethoxy-, propoxy- and butoxyimino; $C_3$–$C_6$-alkenyloxyimino, preferably $C_3$–$C_4$-alkenyloxyimino such as 2-propenyloxyimino, 2-butenyloxyimino, 3-butenyloxyimino; $C_3$–$C_6$-haloalkenyloxyimino, especially $C_3$-haloalkenyloxyimino such as 3,3-dichloro-2-propenyloxyimino, 2-chloro-2-propenyloxyimino, 3-chloro-2-propenyloxyimino and 2,3,3-trichloro-2-propenyloxyimino or benzyloxyimino;

$C_3$–$C_6$-alkenyl such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3 -pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, especially $C_3$–$C_4$-alkenyl such as 2-propenyl, 2-butenyl, 1-methyl-2-propenyl, 2-methyl-2-propenyl, and 3-methyl-2-butenyl and 3-methyl-2-pentenyl;

$C_3$–$C_6$-alkynyl such as 2-propynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3butynyl and 1-ethyl-1-methyl-2-propynyl, especially $C_3$–$C_4$-alkynyl such as 2-propynyl, 2-butynyl and 3-butynyl, it being possible for 2-propynyl to carry one to three, and the alkenyl and remaining alkynyl groups to carry one to five halogen atoms, especially fluorine and chlorine;

phenyl which is unsubstituted or substituted one to three times by $C_1$–$C_4$-alkyl such as methyl, ethyl, propyl, butyl or $C_1$–$C_4$-alkoxy such as methoxy, ethoxy, propoxy, butoxy or one to five times by halogen, especially fluorine and chlorine;

—N=$CR^6R^7$ where $R^6$ and $R^7$ have the following meanings:

$C_1$–$C_{20}$-alkyl, preferably $C_1$–$C_{15}$-alkyl, especially $C_1$–$C_{10}$-alkyl as mentioned above, which can carry phenyl, $C_1$–$C_4$-alkoxy as mentioned above and/or $C_1$–$C_4$-alkylthio as mentioned above;

phenyl, or together $C_3$–$C_{12}$-alkylene, preferably $C_4$–$C_7$-alkylene, which can carry one to three $C_1$–$C_3$-alkyl groups, preferably methyl or ethyl groups;

—$OR^8$ where $R^8$ has the following meanings: hydrogen, the cation of an alkali metal such as sodium or potassium, the cation of an alkaline earth metal such as magnesium or calcium, ammonium or an organic ammonium ion such as tri-($C_1$–$C_4$)-alkylammonium, especially triethylammonium and tributylammonium.

$R^2$ and $R^3$ $C_1$–$C_4$-alkyl such as methyl, ethyl, propyl, 1-methylethyl, butyl, 1-methylpropyl, 2-methylpropyl and 1,1-dimethylethyl;

$C_1$–$C_2$-haloalkyl such as chloromethyl, dichloromethyl, trichloromethyl, chlorofluoromethyl, fluoromethyl, difluoromethyl, trifluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, especially trifluoromethyl; $C_1$–$C_4$-alkoxy such as methoxy, ethoxy, propoxy, 1-methylethoxy, butoxy, 1-methylpropoxy, 2-methylpropoxy and 1,1-dimethylethoxy;

$C_1$–$C_2$-haloalkoxy such as dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, especially difluoromethoxy;

$C_1$–$C_4$-alkylthio such as methylthio, ethylthio, propylthio, 1-methylethylthio, butylthio, 1-methylpropylthio, 2-methylpropylthio and 1,1-dimethylethylthio;

$R^4$ ethynyl, vinyl, 1-chlorovinyl, 2-chlorovinyl, 1,2-dichlorovinyl, 2,2-dichlorovinyl, 1-bromovinyl, 2-bromovinyl, 1,2-dibromovinyl and 2,2-dibromovinyl;

X oxygen or sulfur;

Z nitrogen or =CH—. p The compounds I are obtained, for example, by reacting a salicylic acid derivative II with a compound III in the presence of a base in a conventional manner.

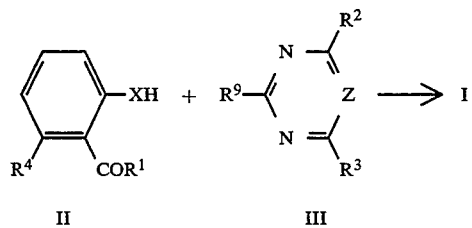

$R^9$ is a nucleofugic leaving group, for example halogen such as chlorine, bromine or iodine, arene- or alkanesulfonyl such as toluenesulfonyl or methanesulfonyl, or another equivalent leaving group.

The compounds II are generally obtained by conventional methods, for example by the Wittig reaction of suitable phosphonium salts with formaldehyde (see T. Eicher et al.: Synthesis (1988) 525 ff.). The resulting intermediates can be modified in a conventional manner by halogenation and elimination and finally converted into the required products.

Compounds of the formula III with a reactive substituent $R^9$ are known or can easily be obtained by conventional methods.

Bases which can be used are alkali metal or alkaline earth metal hydrides such as NaH or $CaH_2$, alkali metal hydroxides such as NaOH or KOH, alkali metal alcoholates such as potassium tert-butylate, alkali metal carbonates such as $Na_2CO_3$ or $K_2CO_3$, alkali metal amides such as $NaNH_2$ or lithium diisopropylamide, or tertiary amines such as triethylamine. When an inorganic base is used it is possible to add a phase-transfer catalyst such as an organic ammonium salt or a crown either, which often increases the reaction rate.

Where the compounds I are the carboxylic acids and salts I' ($R^1$=$OR^8$), it is possible to prepare from them the other compounds complying with the definition, for example by converting the compounds I' in a conventional manner into an activated form such as a halide, preferably the chloride, or imidazolide, and reacting the latter with an alcohol $R^5OH$ such as ethanol, propargyl alcohol or allyl alcohol, a diazole or triazole such as imidazole or 1,2,4-triazole, or N-hydroxysuccinimide. These two steps can also be simplified by, for example, reacting the carboxylic acid with the hydroxyl compound in the presence of a condensing agent such as carbodiimide or a phosphonic anhydride.

It is also possible to convert the carboxylic acids I'' ($R^8$=H) in a conventional manner into a salt, preferably an alkali metal salt, and to react the latter with a compound $R^{10}$-$R^{5'}$ to give the compounds I. The bases used for the reaction between compounds II and III can also be employed for this reaction. $R^{10}$ in the compound $R^{10}$-$R^{5'}$ is a nucleofugic leaving group such as chlorine, bromine, iodine, arene- or alkanesulfonyl such as toluenesulfonyl or methanesulfonyl, and $R^{5'}$ is one of the radicals mentioned for $R^5$ except unsubstituted or substituted phenyl and —N=$CR^6R^7$.

The compounds $R^{10}$-$R^{5'}$ are known or can be prepared by conventional methods.

The novel herbicidal and growth-regulating compounds I and the agents containing them can be applied, for example in the form of directly sprayable solutions, powders, suspensions, including high-percentage aqueous, oily or other suspensions or dispersions, emulsions, oil dispersions, pastes, dusting or broadcasting agents, or granules, by spraying, atomizing, dusting, broadcasting or watering. The application forms depend on the purposes for which they are used; they ought in every case to ensure the finest possible distribution of the novel active ingredients.

The compounds I are generally suitable for preparing directly sprayable solutions, emulsions, pastes or oil dispersion. Suitable inert additives are mineral oil fractions of medium to high boiling point, such as kerosine or diesel oil, also coaltar oils and oils of vegetable or animal origin, aliphatic, cyclic and aromatic hydrocarbons, e.g. toluene, xylene, paraffin, tetrahydronaphthalene, alkylated naphthalenes or derivatives thereof, methanol, ethanol, propanol, butanol, cyclohexanol, cyclohexanone, chlorobenzene, isophorone or highly polar solvents such as N,N-dimethylformamide, dimethyl sulfoxide, N-methylpyrrolidone and water.

Aqueous application forms can be prepared from emulsion concentrates, dispersions, pastes, wettable powders or water-dispersible granules by adding water. To prepare emulsions, pastes or oil dispersions, the substances can be homogenized, as such or dissolved in an oil or solvent, using wetting agnes, adhesion promoters, dispersants or emulsifiers, in water. However, it is also possible to prepare concentrates which are composed of active substance, wetting agent, adhesion promoter, dispersant or emulsifier and, where appropriate, solvent or oil and which are suitable for dilution with water.

Suitable surfactants are the alkali metal, alkaline earth metal and ammonium salts of aromatic sulfonic acids, such as lignin-, phenol-, naphthalene- and dibutylnaphthalenesulfonic acid, and of fatty acids, alkyl- and alkylarylsulfonates, alkyl sulfates, lauryl ether sulfates fatty alcohol sulfates, and salts of sulfated hexa-, hepta- and octadecanols, and of fatty alcohol glycol ether, products of the condensation of sulfonated naphthalene and naphthalene derivatives with formaldehyde, products of the condensation of naphthalene or naphthalenesulfonic acids with phenol and formaldehyde, polyoxyethylene octylphenol ether, ethoxylated isooctyl-, octyl- or nonylphenol, alkylphenol and tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, lignin-sulfite waste liquors and methylcellulose.

Powders and dusting and broadcasting agents can be prepared by mixing or grinding the active substances together with a solid carrier.

Granules, e.g. coated, impregnated or homogenous granules, can be prepared by binding the active ingredients to solid carriers. Examples of solid carriers are mineral earths such as silica gel, silicic acids, silicates, talc, kaolin, limestone, chalk, bole, loess, clay, dolomite, diatomaceous earth, calcium and magnesium sulfates, magnesium oxide, ground plastics, fertilizers such as ammonium sulfate, ammonium phosphate, ammonium nitrate, ureas and vegetable products such as cereals flour, bark meal, wood meal and nutshell meal, cellulose powders or other solid carriers.

The formulation contain from 0.1 to 95% by weight, preferably from 0.5 to 90% by weight, of active ingredient. The active ingredients are employed in a purity of from 90 to 100%, preferably 95 to 100% (according to the NMR spectrum).

Examples of such formulations are:

I. a solution of 90 parts by weight of compound No. 1 and 10 parts by weight of N-methyl-α-pyrrolidone which is suitable for use in the form of very small drops;

II. a mixture of 20 parts by weight of compound No. 2, 80 parts by weight of xylene, 10 parts by weight of the adduct of 8 to 10 moles of ethylene oxide and 1 mole of oleic acid N-monoethanolamide, 5 parts by weight of calcium dodecylbenzenesulfonate, 5 parts by weight of the adduct of 40 moles of ethylene oxide and 1 mole of castor oil; a fine dispersion of the solution in water is suitable for use.

III. an aqueous dispersion of 20 parts by weight of compound No. 1, 40 parts by weight of cyclohexanone, 30 parts by weight of isobutanol, 20 parts by weight of the adduct of 7 moles of ethylene oxide and 1 mole of isooctylphenol and 10 parts by weight of the adduct of 40 moles of ethylene oxide and 1 mole of castor oil;

IV. an aqueous dispersion of 20 parts by weight of compound No. 2, 25 parts by weight of cyclohexanone, 65 parts by weight of a mineral oil fraction of boiling point 210° to 280° C. and 10 parts by weight of the adduct of 40 moles of ethylene oxide and 1 mole of castor oil;

V. a mixture, ground in a hammer mill, of 20 parts by weight of compound No. 1, 3 parts by weight of sodium diisobutylnaphthalene-α-sulfonate, 17 parts by weight of the sodium salt of a ligninsulfonic acid from a sulfite waste liquor and 60 parts by weight of powdered silica gel; a fine dispersion of the mixture in 20,000 parts by weight of water contains 0.1% by weight of the active ingredient and can be used for spraying.

VI. an intimate mixture of 3 parts by weight of compound No. 2 and 97 parts by weight of finely divided kaolin; this dusting agent contains 3% by weight of active ingredient;

VII. an intimate mixture of 30 parts by weight of compound No. 1, 92 parts by weight of powdered silica gel and 8 parts by weight of liquid paraffin which has been sprayed onto the surface of this silica gel; this formulation confers good adhesion on the active ingredient;

VIII. a stable oily dispersion of 20 parts by weight of compound No. 2, 2 parts by weight of calcium dodecylbenzenesulfonate, 8 parts by weight of fatty alcohol polyglycol ether, 2 parts by weight of the sodium salt of a phenolsulfonic acid/urea/formaldehyde condensate and 68 parts by weight of a liquid paraffin.

The herbicidal and growth-regulating agents or the active ingredients can be applied by a pre-emergence or post-emergence method. If the active ingredients are less well tolerated by certain crops, the application techniques can be such that the herbicidal agents are sprayed so as to avoid as far as possible the leaves of the sensitive crops, while the active ingredients reach the leaves of unwanted plants growing underneath them or the uncovered surface of the soil (post-directed, lay-by).

The application rates of herbicidal active ingredient depends on the aim of the control, the season, the target plants and the stage of growth and range from 0.001 to 3.0, preferably 0.01 to 1.0, kg/ha active substance.

The growth-regulating carboxylic acid derivatives of the formula I can influence, in a variety of ways, virtually all stages of development of a plant and are therefore employed as growth regulators. The variety of actions of the plant growth regulators depends in particular on a) the species and variety of the plants,
b) the time of application, based on the stage of development of the plant and on the season,
c) the site and method of application (e.g. seed dressing, soil treatment, leaf application or trunk injection in the case of trees)
d) climatic factors, e.g. temperatures, amount of precipitation, also length of daylight and intensity of light
e) the soil characteristics (including fertilization),
f) the formulation or application form of the active ingredient and, finally,
g) the concentrations of active substance applied.

Some of the various possible uses of the novel plant growth regulators in crop cultivation, in agriculture and in horticulture are mentioned below.

A. The compounds can be used according to the invention to inhibit greatly the vegetative growth of plants, leading to, in particular, a reduction in the length of growth. The treated plants thus exhibit a stunted growth; in addition, the leaves are darker in color.

Advantageous in practice is a reduced intensity of growth of grasses at the edges of roads, in hedges and on canal banks, and on lawns such as in parks, sportsfields and orchards, ornamental lawns and airports to that the labor- and cost-intensive grasscutting can be reduced.

Also of economic interest is the increase in the resistance to lodging of crops susceptible thereto, such as cereals, corn, sunflowers and soybean. The shortening and strengthening of the stalk caused thereby reduces or eliminates the risk of lodging of plants under unfavorable weather conditions before harvest.

Another important use of growth regulators is to inhibit the length of growth and to alter the ripening time of cotton. This makes possible completely mechanized harvesting of this important crop.

The costs of pruning fruit and other trees can be saved with the growth regulators. In addition, the alternation of fruit trees can be interrupted by growth regulators.

The lateral branching of plants can be increased or inhibited by application of growth regulators. This is of interest when, for example in tobacco plants, the formation of side shoots (suckers) is to be inhibited in favor of leaf growth.

Growth regulators can also be used to increase considerably the resistance of frost of, for example, winter rape. In this case there is, on the one hand, inhibition of the length of growth and the development of a too luxuriant (and thus particularly frost-sensitive) leaf and plant mass. On the other hand, the young rape plants are kept back, after sowing and before the onset of winter frosts, in the vegetative stage of development despite favorable growth conditions. This also eliminates the risk of frost for such plants which are prone to premature breakdown of the inhibition of flowering and to enter the generative phase. It is also advantageous with other crops, e.g. winter wheat, for them to be well tillered by treatment with the novel compounds in the fall but not to be too luxuriant at the start of winter. It is possible in this way to prevent an increased sensitivity to frost and, because of the relatively low leaf and plant mass, infection with various diseases (e.g. fungal disease). Inhibition of vegetative growth additionally allows many crops to be planted more densely so that a higher yield per area can be achieved.

B. The growth regulators can be used to achieve increased yields both of parts of plants and of plant constituents. Thus, for example, it is possible to induce the growth of larger amounts of buds, flowers, leaves, fruit, seed kernels, roots and tubers, to increase the sugar content in sugar beet, sugar cane and citrus fruits, to increase the protein content in cereals or soybean or to stimulate a greater flow of latex from rubber trees.

In this connection, the salicylic acid derivatives I can increase yields by intervening in plant metabolism or by promoting or inhibiting vegetative and/or generative growth.

C. Finally, plant growth regulators can be used to achieve both a shortening or lengthening of the stages of development and an increase or decrease in the rate of ripening of the harvested parts of the plants before or after harvest.

Of economic interest is, for example, the facilitation of harvesting made possible by the concentration in time of the fall or reduction in the adhesion to the tree of citrus fruit, olives or other species and varieties of drupes, pomes and caryopses. The same mechanism, i.e. promotion of the development of separating tissue between the fruit or leaf and stem part of the plant, is also essential for well-controlled defoliation of crop plants such as cotton.

D. Furthermore, growth regulators can be used to reduce the water consumption of plants. This is particularly important for agricultural land which has to be artificially irrigated at high cost, e.g. in arid or semi-arid regions. The novel substances can be used to reduce the intensity of irrigation and thus to make management more economic. The influence of growth regulators is to improve the utilization of the available water because, inter alia,
- the width of opening of the stomata is reduced
- a thicker epidermis and cuticula is formed
- the rooting system is improved and
- the microclimate in the crop is favorably affected by more compact growth.

The active ingredients of the formula I to be used according to the invention can be administered to the crop plants both via the seeds (as seed dressing) and via the soil, i.e. through the roots and, particularly preferably, by spraying on the leaves.

The great compatibility with plants means that the application rate can vary within wide limits.

The amounts of active ingredient generally required for seed treatment are from 0.001 to 50 g, preferably 0.01 to 10 g, per kilogram of seeds.

Doses of from 0.001 to 10 kg/ha, preferably 0.01 to 3 kg/ha, especially 0.01 to 0.5 kg/ha, may generally be regarded as sufficient for treatment of leaves and soil.

In view of the wide variety of application methods, the novel compounds and the agents containing them can also be employed to eradicate unwanted plants in a number of other crops. Examples of suitable crops are the following:

| Botanical name | English name |
| --- | --- |
| *Allium cepa* | cooking onion |
| *Ananas comosus* | pineapple |
| *Arachis hypogaea* | peanut |
| *Asparagus officinalis* | asparagus |
| *Beta vulgaris* spp. *altissima* | sugar beet |
| *Beta vulgaris* spp. *rapa* | fodder beet |
| *Brassica napus* var. *napus* | rape |
| *Brassica napus* var. *napobrassica* | Swedish turnip |
| *Brassica rapa* var. *silvestris* | turnip rape |
| *Camellia sinensis* | tea plant |
| *Carthamus tinctorius* | safflower |
| *Carya illinoinensis* | pecan nut |
| *Citrus limon* | lemon |
| *Citrus sinensis* | orange |
| *Coffea arabica (Coffea canephora, Coffea liberica)* | coffee |
| *Cucumis sativus* | cucumber |
| *Cynodon dactylon* | Bermuda grass |
| *Daucus carota* | carrot |
| *Elaeis guineensis* | oil palm |
| *Fragaria vesca* | strawberry |
| *Glycine max* | soybean |
| *Gossypium hirsutum (Gossypium arboreum, Gossypium herbaceum, Gossypium vitifolium)* | cotton |
| *Helianthus annuus* | sunflower |
| *Hevea brasiliensis* | para rubber tree |
| *Hordeum vulgare* | barley |
| *Humulus lupulus* | hops |
| *Ipomoea batatas* | sweet potatoes |
| *Juglans regia* | walnut |
| *Lens culinaris* | lentil |
| *Linum usitatissimum* | flax |
| *Lycopersicon lycopersicum* | tomato |
| *Malus* spp. | apple |
| *Manihot esculenta* | cassava |
| *Medicago sativa* | alfalfa |
| *Musa* spp. | bananas |
| *Nicotiana tabacum (N. rustica)* | tobacco |
| *Olea europaea* | olive |
| *Oryza sativa* | rice |
| *Phaseolus lunatus* | lima bean |
| *Phaseoulus vulgaris* | bush bean |
| *Picea abies* | spruce |
| *Pinus* spp. | pines |
| *Pisum sativum* | garden pea |
| *Prunus avium* | sweet cherry |
| *Prunus persica* | peach |
| *Pyrus communis* | pear |
| *Ribes sylvestre* | redcurrant |
| *Ricinus communis* | castor oil |
| *Saccharum officinarum* | sugar cane |
| *Secale cereale* | rye |
| *Solanum tuberosum* | potato |
| *Sorghum bicolor (S. vulgare)* | sorghum |
| *Theobroma cacao* | cocoa |
| *Trifolium pratense* | red clover |
| *Triticum aestivum* | wheat |
| *Triticum durum* | durum wheat |
| *Vicia faba* | horse bean |
| *Vitis vinifera* | grapevine |
| *Zea mays* | corn |

To extend the spectrum of action and to achieve synergistic effects, the novel compounds I can be mixed and applied together with many representatives of other groups of herbicides or growth regulators. Examples of suitable mixing partners are diazines, 4H-3,1-benzoxazine derivatives, benzothiadiazinones, 2,6-dinitroanilines, N-phenylcarbamates, thiocarbamates, halo carboxylic acids, triazines, amides, ureas, diphenyl ethers, triazinones, uracils, benzofuran derivatives, cyclohexane-1,3-dione derivatives, quinolinecarboxylic acid derivatives, sulfonylureas, aryloxy- and hetaryloxyphenoxypropionic acids and the salts, esters and amides thereof, and others.

It may also be beneficial to apply the compounds I, alone or in combination with other herbicides, mixed together with other crop protection agents, for example with agents for controlling pests or phytopathogenic fungi or bacteria. Also of interest is the miscibility with mineral salt solutions which can be employed to eliminate deficiencies in nutrients and trace elements. It is also possible to add non-phytotoxic oils and oil concentrates.

Synthesis examples

The method given in the following synthesis examples were used, with appropriate modification of the starting compounds, to obtain other compounds I. The compounds obtained in this way are listed, with physical data, in the table which follows. Compounds without these data can be synthesized in a similar manner to the corresponding starting compounds. The structures given in the table describe particularly preferred active ingredients of the formula I.

EXAMPLE 1

Ethyl 2-(4,6-dimethoxy-2-pyrimidyloxy)-6-vinylbenzoate (see Table, No. 1)

a) Ethyl 2-hydroxy-6-vinylbenzoate

A solution of 12.7 g of sodium carbonate in 115 ml of water was added dropwise, while stirring vigorously at room temperate, to 33.8 g of (3-acetoxy-2-ethoxycarbonylbenzyl)triphenylphosphonium bromide (e.g. Eicher et al. Synthesis (1988) 525) in 264 ml of 36.5% by weight aqueous formaldehyde solution. The reaction mixture was stirred at 55° C. for 6 h and then poured into ice-water at pH 1 (hydrochloric acid) and extracted with ethyl acetate, after which the combined organic phases were dried over sodium sulfate and concentrated under reduced pressure. Further purification was carried out by chromatography on silica gel with toluene-/ethyl acetate (20:1) as eluent.

Yield: 4.5 g b) Ethyl 2-(4,6-dimethoxy-2-pyrimidyloxy)-6-vinylbenzoate

A solution of 1.5 g of the product obtained from a), 50 ml of dimethyl sulfoxide and 0.9 g of potassium tert-butylate was stirred for one hour, then 1.7 g of 4,6-dimethoxy-2-methylsulfonylpyrimidine were added, and the mixture was stirred for a further twelve hours, poured into ice-water at pH 1 (hydrochloric acid) and then extracted with ethyl acetate. The organic phase was washed with water, dried over sodium sulfate and evaporated under reduced pressure.

Yield: 2.1 g

EXAMPLE 2

2-(4,6-Dimethoxy-2-pyrimidyloxy)-6-vinylbenzoic acid (see Table, No. 2)

a) 2-Hydroxy-6-vinylbenzoic acid

A solution of 3 g of ethyl 2-hydroxy-6-vinylbenzoate (see Example 1a), 150 ml of methanol and 45 ml of 10% by weight sodium hydroxide solution was boiled for 8 h. It was then poured into ice-water at pH 1 (hydrochloric acid) and extracted with ethyl acetate, and the solution was dried over sodium sulfate and evaporated under reduced pressure.

Yield: 2.3 g b) 2-(4,6-Dimethoxy-2-pyrimidyloxy)-6-vinylbenzoic acid

A solution of 3.14 g of potassium tert-butylate, 2.3 g of the product obtained under a) and 100 ml of dimethyl sulfoxide was stirred at room temperature for 30 min, then 3.05 g of 4,6-dimethoxy-2-methylsulfonylpyrimidine were added and the mixture was stirred for a further 12 h. It was then poured into ice-water at pH 2 (phosphoric acid) and extracted with ethyl acetate. The resulting organic phase was washed with water, dried over sodium sulfate and evaporated under reduced pressure.

Yield: 3.2 g tion of at least the above-ground parts and 0 means no damage or normal growth.

The plants used in the glasshouse tests comprised the following species:

| Abbreviation | Latin name | English name |
| --- | --- | --- |
| ALOMY | *Alopecurus myosuroides* | blackgrass |
| GALAP | *Galium aparine* | catchweed bedstraw |
| POLPE | *Polygonum persicaria* | ladysthumb |
| SOLNI | *Solanum nigrum* | black night-shade |
| TRZAS | *Triticum aestivum* | spring wheat |

TABLE

Salicylic acid derivatives I (with $R^3 = OCH_3$)

| Comp. No. | $R^1$ | $R^2$ | $R^4$ | X | Z | Phys. data* |
| --- | --- | --- | --- | --- | --- | --- |
| 01) | Ethoxy | OCH$_3$ | Vinyl | O | CH | m.p. = 77–79° C. |
| 02) | OH | OCH$_3$ | Vinyl | O | CH | m.p. = 118–121° C. |
| 03) | 2-Propaniminoxy | OCH$_3$ | Vinyl | O | CH | |
| 04) | Methylthiomethyloxy | OCH$_3$ | Ninyl | O | CH | |
| 05) | Propargyloxy | OCH$_3$ | Vinyl | O | CH | |
| 06) | OH | OCH$_3$ | Vinyl | O | CH | |
| 07) | OH | OCH$_3$ | Vinyl | O | CH | |
| 08) | OH | OCH$_3$ | Vinyl | O | CH | |
| 09) | Methoxy | OCH$_3$ | Vinyl | O | CH | |
| 10) | Allyloxy | OCH$_3$ | Vinyl | O | CH | |
| 11) | Phenoxy | OCH$_3$ | Vinyl | O | CH | |
| 12) | Succinimidoxy | OCH$_3$ | Vinyl | O | CH | |
| 13) | Cyanomethoxy | OCH$_3$ | Vinyl | O | CH | |
| 14) | OH | OCH$_3$ | 2,2-Dibromovinyl | O | CH | |
| 15) | OH | OCH$_3$ | 1-Bromovinyl | O | CH | |
| 16) | OH | OCH$_3$ | 2-Bromovinyl | O | CH | |
| 17) | Ethoxy | OCH$_3$ | 3-Bromovinyl | O | CH | |
| 18) | Propargyloxy | OCH$_3$ | Ethynyl | O | CH | |
| 19) | OH | OCH$_3$ | 2-Chlorovinyl | O | CH | |
| 20) | Ethoxy | OCH$_3$ | 2-Chlorovinyl | O | CH | |
| 21) | OH | OCH$_3$ | 1-Chlorovinyl | O | CH | |
| 22) | Methoxy | OCH$_3$ | Ethynyl | O | CH | |
| 23) | Ethoxy | OCH$_3$ | Ethynyl | O | CH | |
| 24) | OH | OCH$_3$ | Ethynyl | O | CH | |
| 25) | 2-Propaniminoxy | OCH$_3$ | Ethynyl | O | CH | |
| 26) | Benzyloxy | OCH$_3$ | Ethynyl | O | CH | |
| 27) | Ethoxycarbonylmethoxy | OCH$_3$ | Vinyl | O | CH | |
| 28) | 1-Imidazolyloxy | OCH$_3$ | Vinyl | O | CH | |
| 29) | 2-(Methoxyimino)-ethoxy | OCH$_3$ | Vinyl | O | CH | |
| 30) | 2-(Ethoxyimino)-propoxy | OCH$_3$ | Vinyl | O | CH | |
| 31) | 2-(3-Allyloxyimino)-ethoxy | OCH$_3$ | Vinyl | O | CH | |

*m.p.: melting point

Examples of herbicidal use

The herbicidal action of a compound I was shown by glasshouse test:

The test plants were grown in plastic flowerpots with a capacity of 300 cm$^3$ containing loamy sand with about 3% humus as substrate. The seeds of the test plants were sown separately according to species.

For post-emergence treatment, the test plants were grown to a height of 3 to 15 cm, depending on the species, and only then treated with the active ingredients suspended or emulsified in water. For this purpose, the test plants were either sown directly and grown in the same vessels or they were germinated separately and transplanted into the test vessels a few days before the treatment. The application rate for post-emergence treatment was 0.06 kg/ha active ingredient.

The test vessels were placed in a glasshouse at 20° to 35° C. for heat-loving species and at 10° to 25° C. for those preferring a more temperate climate. The tests lasted 2 to 4 weeks during which the plants were tended and their reaction to the individual treatments was evaluated.

Evaluation was on a scale from 0 to 100, where 100 means no emergence of the plants or complete destruc- Compound 2 (see table) employed at 0.06 kg/ha by the post-emergence method very effectively controlled unwanted broad-leaved plants.

The test plants received the following damage:

TABLE

Examples of the control of unwanted broad-leaved plants and compatibility with a crop (TRZAS) on post-emergence application of 0.06 kg/ha active substance in a glasshouse Test plants and damage [%]

| TRZAS | SOLNI | GALAP | POLPE | ALOMY |
| --- | --- | --- | --- | --- |
| 10 | 85 | 95 | 90 | 90 |

We claim:

1. A compound of the formula IV

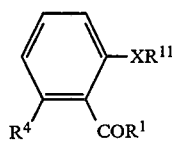

where
R$^1$ is succinimidoxy; a 5-membered heteroaromatic radical which contains two or three nitrogen atoms which can carry one or two halogen atoms and/or one or two of the following: C$_1$–C$_4$-alkyl, C$_1$–C$_4$-haloalkyl, C$_1$–C$_4$-alkoxy, C$_1$–C$_4$-haloalkoxy and/or C$_1$–C$_4$-alkylthio;

R$^4$ is ethynyl or vinyl which can carry one to three halogen atoms;

R$^{11}$ is hydrogen, acetyl or methyl, and

X is oxygen or sulfur.

2. A compound of the formula IV as defined in claim 1, wherein R$^4$ is vinyl.

* * * * *